United States Patent
Rege et al.

(10) Patent No.: US 9,561,160 B2
(45) Date of Patent: Feb. 7, 2017

(54) ORAL CARE COMPOSITION AND PROCESSES FOR PREPARING SAME

(71) Applicant: Colgate-Palmolive Company, New York, NY (US)

(72) Inventors: Aarti Rege, East Windsor, NJ (US); David F. Suriano, Edison, NJ (US); Richard Sullivan, Atlantic Highlands, NJ (US); Ricardo Couso, Hillsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/775,125

(22) PCT Filed: Mar. 15, 2013

(86) PCT No.: PCT/US2013/032375
§ 371 (c)(1),
(2) Date: Sep. 11, 2015

(87) PCT Pub. No.: WO2014/143017
PCT Pub. Date: Sep. 18, 2014

(65) Prior Publication Data
US 2016/0038385 A1 Feb. 11, 2016

(51) Int. Cl.
*A61Q 11/00* (2006.01)
*A61K 8/06* (2006.01)
*A61K 8/25* (2006.01)
*A61K 8/34* (2006.01)
*A61K 8/368* (2006.01)
*A61K 8/44* (2006.01)
*A61K 8/46* (2006.01)
*A61K 8/73* (2006.01)
*A61K 8/86* (2006.01)
*A61K 8/90* (2006.01)
*A61K 8/41* (2006.01)
*A61K 8/49* (2006.01)

(52) U.S. Cl.
CPC ............. *A61K 8/062* (2013.01); *A61K 8/25* (2013.01); *A61K 8/345* (2013.01); *A61K 8/368* (2013.01); *A61K 8/416* (2013.01); *A61K 8/442* (2013.01); *A61K 8/463* (2013.01); *A61K 8/49* (2013.01); *A61K 8/73* (2013.01); *A61K 8/731* (2013.01); *A61K 8/86* (2013.01); *A61K 8/90* (2013.01); *A61Q 11/00* (2013.01); *A61K 2800/262* (2013.01); *A61K 2800/30* (2013.01); *A61K 2800/592* (2013.01); *A61K 2800/594* (2013.01); *A61K 2800/596* (2013.01)

(58) Field of Classification Search
CPC ....... A61Q 11/00; A61K 2300/00; A61K 8/90; A61K 8/731; A61K 9/08; A61K 47/10; A61K 8/062
See application file for complete search history.

(56) References Cited

U.S. PATENT DOCUMENTS

| | | | | |
|---|---|---|---|---|
| 4,456,585 A * | 6/1984 | Hayes et al. | ......... | A61K 8/0237 424/49 |
| 4,973,472 A * | 11/1990 | Morisaki | ............... | A61K 8/0216 424/48 |
| 5,130,122 A * | 7/1992 | Tabibi | ...................... | A61K 8/06 424/49 |
| 5,178,869 A * | 1/1993 | Ebine | ................... | A61K 8/4926 222/192 |
| 5,283,056 A * | 2/1994 | Chung | ................... | A61K 8/062 424/49 |
| 5,628,985 A | 5/1997 | Stiller et al. | | |
| 5,885,556 A | 3/1999 | Lukacovic et al. | | |
| 5,972,312 A * | 10/1999 | Tanii | ..................... | A61K 8/416 424/49 |
| 6,042,812 A * | 3/2000 | Sanker | ..................... | A61K 8/21 424/49 |
| 2004/0126331 A1 | 7/2004 | Corcoran et al. | | |
| 2011/0280814 A1 | 11/2011 | Haught et al. | | |
| 2012/0003162 A1 | 1/2012 | Mordas et al. | | |
| 2012/0082628 A1 | 4/2012 | Haught et al. | | |
| 2013/0224126 A1 | 8/2013 | Lewus et al. | | |

FOREIGN PATENT DOCUMENTS

| | | | | |
|---|---|---|---|---|
| GB | WO 2012019896 | * | 2/2012 | ............... A61K 8/06 |
| IN | WO 2011017633 | * | 2/2011 | ............... A61K 8/19 |

OTHER PUBLICATIONS

International Search Report and Written Opinion in International Application No. PCT/US2013/032375, mailed Nov. 5, 2013.

* cited by examiner

*Primary Examiner* — Frederick Krass
*Assistant Examiner* — Tracy Liu

(57) ABSTRACT

Described herein are processes for preparing an alcohol-free aqueous liquid toothpaste composition which is usable as a mouthwash, the liquid toothpaste being an oil-in-water emulsion with a clear appearance.

29 Claims, No Drawings

ORAL CARE COMPOSITION AND PROCESSES FOR PREPARING SAME

BACKGROUND

It has been observed that the majority of conventional mouthwash formulations (approximately 95% of conventional formulations) contain a high percentage of ethanol, with concentrations ranging from about 10% to 30%. The ethanol is used not only as a disinfectant, but also as a solvent to dissolve additives (such as flavour oils) which are insoluble in water.

However, making a clear oil-in-water emulsion without alcohol but which contains high levels of a water-insoluble flavouring agent is a challenging task, with the dispersion of a high concentration of water-insoluble flavouring agent in a water-based system being difficult to achieve.

A need still exists for an alcohol-free aqueous oral care composition which contains a high level of water-insoluble flavouring agent, but which has a uniform homogenous clear appearance.

It would also be desirable for such a composition to provide the benefits of both a mouthwash and a toothpaste.

SUMMARY

A first aspect of the present invention provides a process for preparing an alcohol-free aqueous liquid toothpaste composition which is usable as a mouthwash, the liquid toothpaste being an oil-in-water emulsion with a clear appearance and a viscosity of between 60 and 550 cps, the process comprising:
(i) preparing a first premix by combining at least one gum with a first humectant in a first vessel;
(ii) preparing a second premix by:
  adding a betaine surfactant, a polysorbate surfactant, and a water-insoluble flavouring agent to a second vessel containing an alkylene glycol;
  mixing the contents of the second vessel; and
  adding an anionic surfactant to the second vessel;
(iii) preparing a third premix by combining water, a preservative, and an active agent in a third vessel;
(iv) adding the first premix to a fourth vessel containing preheated water and mixing the contents of the fourth vessel;
(v) adding a second humectant to the fourth vessel and mixing;
(vi) adding a nonionic block copolymer to the fourth vessel and mixing;
(vii) adding the third premix to the fourth vessel and mixing; and
(viii) adding the second premix to the fourth vessel and mixing.

Optionally, the process further comprises, after step (viii), the step of:
(ix) adding silica to the fourth vessel and mixing.

Optionally, the second premix is an oil-phase premix, and the mixing in step (viii) produces an oil-in-water emulsion.

In some embodiments, the composition has an optical density of less than 0.1 at 500 nm. In some embodiments, the composition has an optical density of less than 0.075 at 500 nm. In some embodiments, the composition has an optical density of less than 0.06 at 500 nm.

Optionally, the flavouring agent is present in an amount of 0.2 wt. % to 10 wt. % based on the total weight of the composition. Further optionally, the flavouring agent is present in an amount of 5 wt. % to 10 wt. % based on the total weight of the composition; or the flavouring agent is present in an amount of 0.5 wt. % to 5 wt. %, optionally 0.5 wt. % to 2 wt. %, based on the total weight of the composition Optionally, the first humectant is present in an amount of between 5 wt. % and 20 wt. % based on the total weight of the composition. Further optionally, the first humectant is present in an amount of between 7 wt. % and 12 wt. % based on the total weight of the composition. Still further optionally, the first humectant is present in an amount of about 9 wt. % based on the total weight of the composition Optionally, the second humectant is present in an amount of between 15 wt. % and 45 wt. % based on the total weight of the composition. Further optionally, the second humectant is present in an amount of between 25 wt. % and 35 wt. % based on the total weight of the composition. Still further optionally, the second humectant is present in an amount of about 30 wt. % based on the total weight of the composition.

Optionally, the first humectant and the second humectant are independently selected from sorbitol, glycerin, propylene glycol, and combinations thereof.

Optionally, the first humectant is glycerin.

Optionally, the second humectant is sorbitol.

Optionally, the total amount of the at least one gum is 0.01 wt. % to 2 wt. % based on the total weight of the composition. Further optionally, the total amount of the at least one gum is 0.03 wt. % to 1 wt. % based on the total weight of the composition. Still further optionally, the total amount of the at least one gum is 0.06 wt. % to 0.55 wt. % based on the total weight of the composition.

Optionally, the at least one gum is selected from gum-type colloidal polymers and cellulosic polymers, and combinations thereof.

Optionally, the gum-type colloidal polymer is selected from agar, agarose, albumin, algae colloid, alginates, alginic acid and salts thereof, amber, ammoniac, amylopectins, arabinans, arabinogalactan, arabinoxylans, asafetida, bdellium, carageenans, casein, chicle, collagen, copal, curdlan, dermatin sulfate, dextrans, cross-linked dextrans, dextrin, emulsan, gelatin, fenugreek, frankincense, furcellarans, galactoglucomannans, galactomannans, gamboge, gellan, gellan gum, glucomannans, glycogens, guar, guar gum, hydroxypropylated guar gums, carboxymethyl guar gum, carboxymethyl(hydroxypropyl) guar gum, hydroxyethyl guar gum, gum arabic, gum elastic, gum ghatti, gum karaya, gum tragancanth (tragacanthin), heparin, hyaluronic acid, India rubber, inulin, karaya gum, keratin sulfate, konjac flour, konjac mannan, labdanum, laminarans, laurdimonium, laxseed saccharide (acidic), levan, locust bean gum, myrrh, okra gum, pectic acids, pectin, polydextrose, polyquaternium-4, polyquaternium-10, polyquaternium-28, protopectins, psyllium seed gum, pullulan, quince seed gum, sodium hyaluronate, raffinose, rhamsan, scleroglucan, sodium alginate, stachylose, starch from rice, corn, potato or wheat, tapioca starch, succinoglycan, tamarind seed gum, trant gum, water-soluble soybean polysaccharide, whelan, xanthan, xanthan gum, xylans, xyloglucans, and mixtures thereof Optionally, the cellulosic polymer is selected from cellulose; methyl cellulose; ethyl cellulose; propyl cellulose; butyl cellulose; carboxymethyl cellulose; carboxyethyl cellulose; carboxymethyl methyl cellulose; carboxyethyl ethyl cellulose; carboxyethyl methyl cellulose; carboxymethyl ethyl cellulose; hydroxyalkyl cellulose; hydroxymethyl cellulose; hydroxyethyl cellulose; hydroxypropyl cellulose; hydroxybutyl cellulose; hydroxymethyl methyl cellulose; hydroxyethyl methyl cellulose; hydroxypropyl methyl cellulose; hydroxybutyl methyl cellulose; hydroxymethyl ethyl cellulose; hydroxyethyl ethyl cellulose; hydroxypropyl ethyl cellulose; hydroxybutyl ethyl cellulose; hydroxymethyl propyl cellulose; hydroxyethyl propyl cellulose; hydroxypropyl propyl cellulose; hydroxybutyl propyl cellulose; hydroxymethyl butyl cellulose; hydroxyethyl butyl cellulose; hydroxypropyl butyl cellulose; hydroxybutyl butyl cellulose; hydroxypropyl oxyethyl cellulose; steardimonium hydroxyethyl cellulose; cocodimonium hydroxypropyl oxyethyl cellulose; sodium carboxymethyl cellulose; nitrocellulose; sodium cellulose sulfate; chondroitin; chitin; chitosan; chitosan pyrrolidone carboxylate; chitosan glycolate chitosan lactate and mixtures thereof.

Optionally, the at least one gum comprises xanthan gum and a cellulosic polymer. Further optionally, the cellulosic polymer is sodium carboxymethyl cellulose.

Optionally, the betaine surfactant is present in an amount of between 1 wt. % and 10 wt. % based on the total weight of the composition.

Optionally, the betaine surfactant is cocoamidoethyl betaine, cocoamidopropyl betaine, lauramidopropyl betaine or mixtures thereof. Further optionally, the betaine surfactant is cocoamidopropyl betaine.

Optionally, the polysorbate surfactant is present in an amount of between 0.5 wt. % and 3 wt. % based on the total weight of the composition.

Optionally, the polysorbate surfactant is selected from polysorbate 20, polysorbate 40, polysorbate 60, polysorbate 80 and mixtures thereof. Further optionally, the polysorbate surfactant is polysorbate 20.

Optionally, the alkylene glycol is present in an amount of between 5 wt % and 10 wt % based on the total weight of the composition.

Optionally, the alkylene glycol is selected from ethylene glycol, propylene glycol, dipropylene glycol, hexylene glycol and mixtures thereof. Further optionally, the alkylene glycol is propylene glycol.

Optionally, the anionic surfactant is present in an amount of between 0.5 wt. % and 2 wt. % based on the total weight of the composition.

Optionally, the anionic surfactant is sodium lauryl sulfate.

Optionally, the preservative is present in an amount of between 0.1 wt. % and 1 wt. % based on the total weight of the composition.

Optionally, the preservative is selected from parabens, potassium sorbate, benzyl alcohol, phenoxyethanol, polyaminopropyl biguanide, caprylic acid, sodium benzoate and mixtures thereof. Further optionally, the preservative is sodium benzoate.

Optionally, the active agent is selected from an antimicrobial agent, a tartar control agent, a fluoride ion source, a breath-freshening agent, an antioxidant, a saliva stimulating agent, an antiplaque agent, a desensitizing agent, and mixtures thereof.

Optionally, the active agent comprises an antimicrobial agent, the antimicrobial agent being selected from cetylpyridinium chloride, triclosan, zinc ion sources, stannous ion sources, chlorhexidine, benzalkonium chloride, and mixtures thereof.

Optionally, the active agent comprises a tartar control agent, the tartar control agent being selected from monobasic sodium phosphate, dibasic sodium phosphate, tribasic sodium phosphate, sodium tripolyphosphate, sodium tetrapolyphosphate, mono-, di-, tri- and tetrasodium pyrophosphates, sodium trimetaphosphate, sodium hexametaphosphate, monobasic potassium phosphate, dibasic potassium phosphate, tribasic potassium phosphate, potassium tripolyphosphate, potassium tetrapolyphosphate, mono-, di-, tri- and tetrapotassium pyrophosphates, potassium trimetaphosphate, potassium hexametaphosphate, monobasic ammonium phosphate, dibasic ammonium phosphate, tribasic ammonium phosphate, ammonium tripolyphosphate, ammonium tetrapolyphosphate, mono-, di-, tri- and tetraammonium pyrophosphates, ammonium trimetaphosphate, ammonium hexametaphosphate and mixtures thereof.

Optionally, the nonionic block copolymer is present in an amount of between 0.25 wt. % and 2 wt. % based on the total weight of the composition.

Optionally, the nonionic block copolymer is a poloxamer.

Optionally, one or more of a colorant and a sweetener is added to the third premix in step (iii).

Optionally, the preheated water in step (iv) is heated to between 66° C. and 99° C. (between 150° F. and 210° F.). Further optionally, the preheated water in step (iv) is heated to between 77° C. and 88° C. (between 170° F. and 190° F.). Still further optionally, the preheated water in step (iv) is heated to about 83° C. (about 180° F.).

Optionally, the water in step (iii) is heated to between 66° C. and 99° C. (between 150° F. and 210° F.). Further optionally, the water in step (iii) is heated to between 77° C. and 88° C. (between 170° F. and 190° F.). Still further optionally, the water in step (iii) is heated to about 83° C. (about 180° F.).

Optionally, the betaine surfactant, polysorbate surfactant and water-insoluble flavouring agent are added to the third vessel in step (iii) in the following order:
I) betaine surfactant,
II) polysorbate surfactant,
III) flavouring agent.

Optionally, the contents of the fourth vessel in step (iv) are mixed for between 10 minutes and 20 minutes. Further optionally, the contents of the fourth vessel in step (iv) are mixed for about 15 minutes.

Optionally, the mixing of step (iv) is carried out under vacuum at a pressure of from about 25 to about 28 in. Hg.

Optionally, the mixing of step (v) is carried out for between 1 minute and 10 minutes. Further optionally, the mixing of step (v) is carried out for about 5 minutes.

Optionally, the mixing of step (vi) is carried out for between 10 minutes and 20 minutes. Further optionally, the mixing of step (vi) is carried out for about 15 minutes.

Optionally, the mixing of step (vi) is carried out under vacuum at a pressure of from about 25 to about 28 in. Hg.

Optionally, the mixing of step (vii) is carried out for between 5 minutes and 15 minutes. Further optionally, the mixing of step (vii) is carried out for about 10 minutes.

Optionally, the mixing of step (viii) is carried out for between 1 minute and 10 minutes. Further optionally, the mixing of step (viii) is carried out for about 5 minutes.

Optionally, the mixing of step (ix) is carried out for between 1 minute and 10 minutes. Further optionally, the mixing of step (ix) is carried out for about 5 minutes.

A second aspect of the present invention provides an alcohol-free aqueous liquid toothpaste composition produced by the process of the present invention.

A third aspect of the present invention provides an alcohol-free aqueous liquid toothpaste composition which is usable as a mouthwash, the liquid toothpaste being an oil-in-water emulsion with a clear appearance and a viscosity of between 100 and 400 cps and comprising at least one gum, a first humectant, a betaine surfactant, a polysorbate surfactant, a water-insoluble flavouring agent, an alkylene glycol, an anionic surfactant, a preservative, an active agent, a second humectant and a nonionic block copolymer.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range.

All references cited herein are hereby incorporated by reference in their entireties. In the event of a conflict in a definition in the present disclosure and that of a cited reference, the present disclosure controls.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition unless otherwise indicated. As referred to herein, "ppm" (parts per million) refers to ppm by weight, unless otherwise indicated. As referred to herein, all ratios refer to weight ratios, unless otherwise indicated.

As used herein, when a composition is described as being "alcohol-free", the term "alcohol-free" means that the composition does not contain a $C_1$-$C_6$ mono-alcohol. Examples of such $C_1$-$C_6$ mono-alcohols include methanol, ethanol, propanols, butanols, pentanols and hexanols. In particular, the compositions of the present invention do not contain ethanol.

The present application is directed towards the preparation of an alcohol-free liquid toothpaste composition which is usable as a mouthwash. The composition can be used to rinse the mouth like a mouthwash (thus killing microbes and providing the "whole mouth" clean and feeling of freshness associated with mouthwash use) and, after expectorating, the remaining composition left in the oral cavity can be used in tooth brushing like a toothpaste (thus delivering the tooth cleaning and therapeutic benefits associated with toothpaste use). The composition thus provides the benefits of both a mouthwash and a toothpaste.

The present inventors have also found that the process of the present invention allows for the preparation of an alcohol-free aqueous liquid toothpaste composition which has a clear appearance, but which can contain a high level of water-insoluble flavouring agent.

In one aspect, the present invention provides a process for preparing an alcohol-free aqueous liquid toothpaste composition which is usable as a mouthwash, the liquid toothpaste being an oil-in-water emulsion with a clear appearance and a viscosity of between 60 and 550 cps, the process comprising:

(i) preparing a first premix by combining at least one gum with a first humectant in a first vessel;

(ii) preparing a second premix by:
 adding a betaine surfactant, a polysorbate surfactant, and a water-insoluble flavouring agent to a second vessel containing an alkylene glycol;
 mixing the contents of the second vessel; and
 adding an anionic surfactant to the second vessel;

(iii) preparing a third premix by combining water, a preservative, and an active agent in a third vessel;

(iv) adding the first premix to a fourth vessel containing preheated water and mixing the contents of the fourth vessel;

(v) adding a second humectant to the fourth vessel and mixing;

(vi) adding a nonionic block copolymer to the fourth vessel and mixing;

(vii) adding the third premix to the fourth vessel and mixing; and (viii) adding the second premix to the fourth vessel and mixing.

In some embodiments, the process further comprises, after step (viii), the step of: (ix) adding silica to the fourth vessel and mixing. In some embodiments, the silica may be a silica abrasive such as such as a precipitated or hydrated silica having a mean particle size of up to about 20 microns, for example Zeodent 105 and Zeodent 114 marketed by J.M. Huber Chemicals Division, Havre de Grace, Md. 21078, Sylodent 783 marketed by Davison Chemical Division of W.R. Grace & Company, Sorbosil AC 43 from PQ Corporation, and mixtures thereof. In some embodiments, the silica may be a silica thickener such as such as Zeodent 115 or Zeodent 165 (both available from Huber Engineered Materials) and DT 267 (available from PPG Industries). In some embodiments, the silica may be a silica which provides a sensory effect to the user, for example Sorbosil BFG 10, BFG50 and BFG 100 (from PQ Corporation) which provides a distinct mouthfeel to the user (e.g. as a "scrubbing" sensation).

In some embodiments, the silica is present in an amount of from 0.05 wt. % to 1 wt. %, or from 0.05 wt. % to 0.5 wt. %, based on the total weight of the composition.

In some embodiments, the second premix is an oil-phase premix, and the mixing in step (viii) produces an oil-in-water emulsion.

In some embodiments, the flavouring agent is present in an amount of 0.2 wt. % to 10 wt. % based on the total weight of the composition. In some embodiments, the flavouring agent is present in an amount of 5 wt. % to 10 wt. %, 6 wt. % to 9 wt. %, or 7 wt. % to 8 wt. %, based on the total weight of the composition. In other embodiments, the flavouring agent is present in an amount of 0.5 wt. % to 5 wt. %, 0.5 wt % to 2 wt. %, 0.7 wt. % to 1.5 wt. %, or 0.8 wt. % to 1 wt %, based on the total weight of the composition. In some embodiments, the flavouring agent is present in an amount of about 0.7 wt. % based on the total weight of the composition.

Any suitable water-insoluble flavouring agent may be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc.

Also encompassed within the suitable flavouring agents herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

In some embodiments, the first humectant is present in an amount of between 5 wt. % and 20 wt. %, between 6 wt. % and 15 wt. %, between 7 wt. % and 12 wt. %, or between 8 wt. % and 10 wt. %, based on the total weight of the composition. In some embodiments, the first humectant is present in an amount of about 9 wt. % based on the total weight of the composition.

In some embodiments, the second humectant is present in an amount of between 15 wt. % and 45 wt. %, between 20 wt. % and 40 wt. %, between 25 wt. % and 35 wt. %, or between 27 wt. % and 33 wt. %, based on the total weight of the composition. In some embodiments, the second humectant is present in an amount of about 30 wt. % based on the total weight of the composition.

In some embodiments, the first humectant and the second humectant are independently selected from sorbitol, glycerin, propylene glycol, and combinations thereof. In some embodiments, first humectant is glycerin. In some embodiments, the second humectant is sorbitol. In some embodiments, the first humectant is glycerin and the second humectant is sorbitol.

In some embodiments the total amount of the at least one gum is 0.01 wt. % to 2 wt. %, 0.02 wt. % to 1.5 wt. %, 0.03 wt. % to 1 wt. %, 0.04 wt. % to 0.8 wt. %, 0.05 to 0.6 wt. %, 0.06 wt. % to 0.55 wt. %, 0.32 wt. % to 0.5 wt. %, or 0.4 wt. % to 0.45 wt. %, based on the total weight of the composition.

In some embodiments, the at least one gum is selected from gum-type colloidal polymers and cellulosic polymers, and combinations thereof.

In some embodiments, the gum-type colloidal polymer is selected from agar, agarose, albumin, algae colloid, alginates, alginic acid and salts thereof, amber, ammoniac, amylopectins, arabinans, arabinogalactan, arabinoxylans, asafetida, bdellium, carageenans, casein, chicle, collagen, copal, curdlan, dermatin sulfate, dextrans, cross-linked dextrans, dextrin, emulsan, gelatin, fenugreek, frankincense, furcellarans, galactoglucomannans, galactomannans, gamboge, gellan, gellan gum, glucomannans, glycogens, guar, guar gum, hydroxypropylated guar gums, carboxymethyl guar gum, carboxymethyl(hydroxypropyl) guar gum, hydroxyethyl guar gum, gum arabic, gum elastic, gum ghatti, gum karaya, gum tragancanth (tragacanthin), heparin, hyaluronic acid, India rubber, inulin, karaya gum, keratin sulfate, konjac flour, konjac mannan, labdanum, laminarans, laurdimonium, laxseed saccharide (acidic), levan, locust bean gum, myrrh, okra gum, pectic acids, pectin, polydextrose, polyquaternium-4, polyquaternium-10, polyquaternium-28, protopectins, psyllium seed gum, pullulan, quince seed gum, sodium hyaluronate, raffinose, rhamsan, scleroglucan, sodium alginate, stachylose, starch from rice, corn, potato or wheat, tapioca starch, succinoglycan, tamarind seed gum, trant gum, water-soluble soybean polysaccharide, whelan, xanthan, xanthan gum, xylans, xyloglucans, and mixtures thereof.

In some embodiments, the cellulosic polymer is selected from cellulose; methyl cellulose; ethyl cellulose; propyl cellulose; butyl cellulose; carboxymethyl cellulose; carboxyethyl cellulose; carboxymethyl methyl cellulose; carboxyethyl ethyl cellulose; carboxyethyl methyl cellulose; carboxymethyl ethyl cellulose; hydroxyalkyl cellulose; hydroxymethyl cellulose; hydroxyethyl cellulose; hydroxypropyl cellulose; hydroxybutyl cellulose; hydroxymethyl methyl cellulose; hydroxyethyl methyl cellulose; hydroxypropyl methyl cellulose; hydroxybutyl methyl cellulose; hydroxymethyl ethyl cellulose; hydroxyethyl ethyl cellulose; hydroxypropyl ethyl cellulose; hydroxybutyl ethyl cellulose; hydroxymethyl propyl cellulose; hydroxyethyl propyl cellulose; hydroxypropyl propyl cellulose; hydroxybutyl propyl cellulose; hydroxymethyl butyl cellulose; hydroxyethyl butyl cellulose; hydroxypropyl butyl cellulose; hydroxybutyl butyl cellulose; hydroxypropyl oxyethyl cellulose; steardimonium hydroxyethyl cellulose; cocodimonium hydroxypropyl oxyethyl cellulose; sodium carboxymethyl cellulose; nitrocellulose; sodium cellulose sulfate; chondroitin; chitin; chitosan; chitosan pyrrolidone carboxylate; chitosan glycolate chitosan lactate and mixtures thereof.

In some embodiments, the gum-type colloidal polymer is present in an amount of between 0.05 wt. % and 0.4 wt. %, between 0.15 wt. % and 0.35 wt. %, or between 0.3 wt. % and 0.35 wt. %, based on the total weight of the composition.

In some embodiments, the cellulosic polymer is present in an amount of between 0.01 wt. % and 0.25 wt. %, between 0.01 wt. % and 0.21 wt. %, between 0.01 wt. % and 0.1 wt. %, or between 0.06 wt. % and 0.1 wt. %, based on the total weight of the composition.

In some embodiments, the at least one gum comprises xanthan gum and a cellulosic polymer. In some embodiments, the at least one gum comprises xanthan gum and the cellulosic polymer sodium carboxymethyl cellulose (sodium CMC).

In some embodiments, the betaine surfactant is present in an amount of between 1 wt. % and 10 wt. %, between 1.25 wt. % and 9.4 wt. %, between 2 wt. % and 8.8 wt. %, or between 2.4 wt. % and 5 wt. %, based on the total weight of the composition.

In some embodiments, the betaine surfactant is an alkyl dimethyl betaine. In some embodiments, the alkyl methyl betaine can be decyl betaine or 2-(N-decyl-N,N-dimethylammonio) acetate, myristyl betaine, palmityl betaine, lauryl betaine, cetyl betaine, stearyl betaine, and the like. The amidobetaines similarly include cocoamidoethyl betaine, cocoamidopropyl betaine, lauramidopropyl betaine and the like. A preferred betaine is cocoamidopropyl betaine, cocoamidoethyl betaine, cocoamidopropyl betaine, lauramidopropyl betaine or mixtures thereof. In some embodiments, the betaine surfactant is cocoamidopropyl betaine (CAP betaine).

In some embodiments, the polysorbate surfactant is present in an amount of between 0.5 wt. % and 3 wt. %, between 0.6 wt. % and 2.9 wt. %, between 0.6 wt. % and 1.64 wt. %, or between 0.6 wt. % and 1.46 wt. %, based on the total weight of the composition.

In some embodiments, the polysorbate surfactant is selected from polysorbate 20, polysorbate 40, polysorbate 60, polysorbate 80 and mixtures thereof. In some embodiments, the polysorbate surfactant is polysorbate 20.

In some embodiments, the alkylene glycol is present in an amount of between 5 wt % and 10 wt %, between 6 wt. % and 9 wt. %, or between 7 wt. % and 8 wt. % based on the total weight of the composition. In some embodiments, the alkylene glycol is present in an amount of about 8 wt. % based on the total weight of the composition.

In some embodiments, the alkylene glycol is selected from ethylene glycol, propylene glycol, dipropylene glycol, hexylene glycol and mixtures thereof. In some embodiments, the alkylene glycol is propylene glycol.

In some embodiments, the anionic surfactant is present in an amount of between 0.5 wt. % and 2 wt. %, between 0.5 wt. % and 1.5 wt. %, between 0.5 wt. % and 1 wt. %, or between 0.6 wt. % and 0.8 wt. % based on the total weight of the composition. In some embodiments, the anionic surfactant is present in an amount of about 0.6 wt. % based on the total weight of the composition.

Anionic surfactants suitable for use in the surfactant system of the present invention include water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, alkyl ethoxy sulfates, monoalkylphosphates, α-olefin sulphonates, higher fatty acid esters of 1,2-dihydroxypropane sulfonate, organic phosphates esters, such as mono- and di-alkylethoxyphosphates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. A preferred anionic surfactant is sodium lauryl sulfate.

In some embodiments, the preservative is present in an amount of between 0.1 wt. % and 1 wt. %, between 0.25 wt. % and 0.75 wt. %, or between 0.4 wt. % and 0.6 wt. % based on the total weight of the composition. In some embodiments, the preservative is present in an amount of about 0.5 wt. % based on the total weight of the composition.

In some embodiments, the preservative is selected from parabens, potassium sorbate, benzyl alcohol, phenoxyethanol, polyaminopropyl biguanide, caprylic acid, sodium benzoate and mixtures thereof. In some embodiments, the preservative is sodium benzoate.

In some embodiments, the active agent is selected from an antimicrobial agent, a tartar control agent, a fluoride ion source, a breath-freshening agent, an antioxidant, a saliva stimulating agent, an antiplaque agent, a desensitizing agent, and mixtures thereof.

In some embodiments, the active agent comprises an antimicrobial agent, the antimicrobial agent being selected from cetylpyridinium chloride (CPC), triclosan, zinc ion sources, stannous ion sources, chlorhexidine, benzalkonium chloride, and mixtures thereof.

In some embodiments, the antimicrobial agent is present in an amount of between 0.001 wt. % and 1 wt. %, 0.01 wt. % and 0.5 wt. %, or 0.05 wt. % and 0.1 wt. % based on the total weight of the composition.

In some embodiments, the active agent comprises a tartar control agent, the tartar control agent being selected from monobasic sodium phosphate, dibasic sodium phosphate, tribasic sodium phosphate, sodium tripolyphosphate, sodium tetrapolyphosphate, mono-, di-, tri- and tetrasodium pyrophosphates, sodium trimetaphosphate, sodium hexametaphosphate, monobasic potassium phosphate, dibasic potassium phosphate, tribasic potassium phosphate, potassium tripolyphosphate, potassium tetrapolyphosphate, mono-, di-, tri- and tetrapotassium pyrophosphates, potassium trimetaphosphate, potassium hexametaphosphate, monobasic ammonium phosphate, dibasic ammonium phosphate, tribasic ammonium phosphate, ammonium tripolyphosphate, ammonium tetrapolyphosphate, mono-, di-, tri- and tetraammonium pyrophosphates, ammonium trimetaphosphate, ammonium hexametaphosphate and mixtures thereof. In some embodiments, the tartar control agent is monobasic sodium phosphate. In some embodiments, the tartar control agent is present in an amount of between 0.5 wt. % and 2 wt. %, between 0.7 wt. % and 1.5 wt. %, or between 0.8 wt. % and 1.2 wt. % based on the total weight of the composition. In some embodiments, the tartar control agent is present in an amount of about 1 wt. % based on the total weight of the composition.

In some embodiments, the active agent comprises a fluoride ion source. Suitable fluoride ion sources include, but are not limited to, stannous fluoride, sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof. Fluoride ion sources may be present at a level of 0.001 wt. % to 10 wt. %, 0.003 wt. % to t 5 wt. %, 0.01 wt. % to 1 wt. %, or about 0.05 wt. % based on the total weight of the composition.

In some embodiments, the active agent comprises a breath-freshening agent. Any orally acceptable breath-freshening agent may be used, including without limitation zinc salts such as zinc gluconate, zinc citrate and zinc chlorite, alpha-ionone and mixtures thereof.

In some embodiments, the active agent comprises an antioxidant. Any orally acceptable antioxidant may be used, including but not limited to butylated hydroxyanisole (BHA), vitamin A, carotenoids, vitamin E, flavonoids, polyphenols, ascorbic acid, herbal antioxidants, chlorophyll, melatonin and mixtures thereof.

In some embodiments, the active agent comprises a saliva stimulating agent. Any orally acceptable saliva stimulating agent may be used, including without limitation food acids such as citric acid, lactic acid, malic acid, succinic acid, ascorbic acid, adipic acid, fumaric acid, tartaric acid and mixtures thereof.

In some embodiments, the active agent comprises an antiplaque agent. Any orally acceptable antiplaque agent may be used, including but not limited to stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

In some embodiments, the active agent comprises a desensitizing agent. Suitable desensitizing agents include, without limitation, potassium tartrate, potassium bicarbonate, potassium oxalate, potassium nitrate, strontium salts and mixtures thereof.

In some embodiments, the nonionic block copolymer is present in an amount of between 0.25 wt. % and 2 wt. %, optionally 0.25 wt. % to 0.9 wt. %, based on the total weight of the composition.

In some embodiments, the nonionic block copolymer is a poloxamer. An example of a poloxamer is Pluronic F-127NF, from BASF.

In some embodiments, one or more of a colorant and a sweetener is added to the third premix in step (iii).

In some embodiments, a sweetener is added to the third premix in step (iii). Suitable sweeteners include dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (such as sodium saccharin), dipeptide-based intense sweeteners, cyclamates and the like. In some embodiments, the sweetener is present in an amount of from 0.001 wt. % to 5 wt. %, 0.005 wt. % to 0.3 wt. %, or 0.05 wt. % to 0.1 wt. % based on the total weight of the composition. In some embodiments, the sweetener is saccharin and may be present in an amount of about 0.05 wt. % based on the total weight of the composition.

In some embodiments, a colorant is added to the third premix in step (iii). Suitable colorants include food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-.DELTA.-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. In certain embodiments, the colorant is FD&C Blue No. 1. Typically, colorants if included are present in very small quantities, for example 0.02 wt. % to 0.15 wt. %, 0.05 wt. % to 0.1 wt. %, 0.06 wt. % to 0.09 wt. %, or about 0.075 wt. % based on the total weight of the composition. In certain embodiments, the colorant may be added as a solution in water, for example the colorant may be added as a 1% solution in water, and the solution added in an amount of between 0.05 wt. % and 0.1 wt. %, between 0.06 wt. % and 0.09 wt. %, or about 0.075 wt. % based on the total weight of the composition.

In some embodiments, the water in the third premix is present in an amount of between 2 wt. % and 15 wt. %, 5 wt. % and 13 wt. %, or 7 wt. % and 12 wt. % based on the total weight of the composition. In some embodiments, the water in the third premix is present in an amount of about 10 wt. % based on the total weight of the composition.

In some embodiments, the flavouring agent is present in an amount of between 0.7 wt. % and 1.5 wt % based on the weight of the composition; the first humectant is present in an amount of between 8 wt. % and 10 wt. % based on the total weight of the composition; the second humectant is present in an amount of between 27 wt. % and 33 wt. % based on the total weight of the composition; the gum-type colloidal polymer is present in an amount of between 0.15 wt. % and 0.35 wt. %; the cellulosic polymer is present in an amount of between 0.01 wt. % and 0.1 wt. % based on the total weight of the composition; the betaine surfactant is present in an amount of between 2 wt. % and 8.8 wt. %, based on the total weight of the composition; the polysorbate surfactant is present in an amount of between 0.6 wt. % and 1.64 wt. % based on the total weight of the composition; the alkylene glycol is present in an amount of between 7 wt. % and 8 wt. % based on the total weight of the composition; the anionic surfactant is present in an amount of between 0.6 wt. % and 0.8 wt. % based on the total weight of the composition; the preservative is present in an amount of between 0.4 wt. % and 0.6 wt. % based on the total weight of the composition; the active agent is present in an amount of between 0.7 wt. % and 1.5 wt. % based on the total weight of the composition; and the non-ionic block copolymer is present in an amount of between 0.25 wt. % to 2 wt. %.

In some embodiments, the betaine surfactant, polysorbate surfactant and water-insoluble flavouring agent are added to the third vessel in step (iii) in the following order:
I) betaine surfactant,
II) polysorbate surfactant,
III) flavouring agent.

In some embodiments, the water in step (iii) is heated to between 66° C. and 99° C. (between 150° F. and 210° F.), between 72° C. and 93° C. (between 160° F. and 200° F.), between 77° C. and 88° C. (between 170° F. and 190° F.), or to about 83° C. (about 180° F.).

In some embodiments, the preheated water in step (iv) is heated to between 66° C. and 99° C. (between 150° F. and 210° F.), between 72° C. and 93° C. (between 160° F. and 200° F.), between 77° C. and 88° C. (between 170° F. and 190° F.), or to about 83° C. (about 180° F.).

In some embodiments, the contents of the fourth vessel in step (iv) are mixed for between 10 minutes and 20 minutes, between 12 minutes and 18 minutes, or for about 15 minutes.

In some embodiments, the mixing of step (iv) is carried out under vacuum at a pressure of from about 25 to about 28 in. Hg.

In some embodiments, the mixing of step (v) is carried out for between 1 minute and 10 minutes, between 2 minutes and 8 minutes, or for about 5 minutes.

In some embodiments, the mixing of step (vi) is carried out for between 10 minutes and 20 minutes, between 12 minutes and 18 minutes, or for about 15 minutes.

In some embodiments, the mixing of step (vi) is carried out under vacuum at a pressure of from about 25 to about 28 in. Hg.

In some embodiments, the mixing of step (vii) is carried out for between 5 minutes and 15 minutes, between 7 minutes and 13 minutes, or for about 10 minutes.

In some embodiments, the mixing of step (viii) is carried out for between 1 minute and 10 minutes, between 2 minutes and 8 minutes, or for about 5 minutes.

In some embodiments, the mixing of step (ix) is carried out for between 1 minute and 10 minutes, between 2 minutes and 8 minutes, or for about 5 minutes.

In another aspect, the present invention provides an alcohol-free aqueous liquid toothpaste composition produced by the process as described above.

In a further aspect, the present invention provides an alcohol-free aqueous liquid toothpaste composition which is usable as a mouthwash, the liquid toothpaste being an oil-in-water emulsion with a clear appearance and a viscosity of between 100 and 400 and comprising at least one gum, a first humectant, a betaine surfactant, a polysorbate surfactant, a water-insoluble flavouring agent, an alkylene glycol, an anionic surfactant, a preservative, an active agent, a second humectant and a nonionic block copolymer. The gums, humectants, surfactants, flavouring agent, alkylene glycol, preservative, active agent and nonionic block copolymer may be present in the composition in the various amounts as described above.

EXAMPLES

Example 1

Various compositions were prepared using the process of the present invention. These compositions are shown in Table 1.

Method

To make the first premix, the recited amounts of the gums were added to the glycerin. To make the second premix, the recited amounts of (in order) the betaine, polysorbate 20, and flavor were added to the propylene glycol and mixed on a bench mixer, followed by addition of the sodium lauryl sulfate. To make the third premix, to the hot deionized water (at 83° C. i.e. 180° F.) the following ingredients were added (in order) using a bench mixer: sodium benzoate, sodium phosphate (slowly), saccharin and CPC.

The Qs formula amount of hot deionized water at 83° C. (180° F.) was added to a pre-heated 1 kilo ROSS mixer. The first premix was then added by hand, and the mixture was mixed under vacuum at a pressure of from about 25 to about 28 in. Hg for 15 minutes. The sorbitol was then added and the mixture was mixed for 5 minutes. The poloxamer was then added by hand and the mixture was mixed under vacuum at a pressure of from about 25 to about 28 in. Hg for 15 minutes. The third premix was then added and the mixture was mixed for 10 minutes. The second premix was then added and the mixture was mixed vigorously for 5 minutes. If using, the silica was then added and the mixture was mixed for 5 minutes.

The compositions were stored for 1 week at 49° C., and their appearance, pH, viscosity and Shakefoam value were recorded.

To obtain a Shakefoam value, a sample is dissolved in water to form a 0.1% solution. Each solution is then poured into a graduated cylinder and placed into an inversion machine set to invert and return to its original position 30 times. The foam volume (in milliliters) is then recorded as the Shakefoam value.

The compositions were then inspected again after storing for a total of 2 months at 49° C., and the distribution of the silica (if present) was recorded, along with any colour change of the compositions.

TABLE 1

|  | A | B | C |
|---|---|---|---|
| Part 1 | | | |
| Qs Hot Deionised Water | 36.435 | 30.375 | 34.785 |
| Part 2- First Premix | | | |
| Glycerine | 9.000 | 9.000 | 9.000 |
| Xanthan Gum | 0.170 | 0.350 | 0.050 |
| Sodium CMC Gum | 0.070 | 0.100 | 0.010 |
| Part 3 | | | |
| Sorbitol | 30.000 | 30.000 | 30.000 |
| Pluronic F-127NF (Poloxomer) | 0.850 | 0.250 | 0.250 |
| Part 4- Third Premix | | | |
| Hot Deionised Water | 10.000 | 10.000 | 10.000 |
| Sodium Benzoate | 0.500 | 0.500 | 0.500 |
| Monobasic Na Phosphate | 1.000 | 1.000 | 1.000 |
| Saccharin | 0.050 | 0.050 | 0.050 |
| CPC | 0.050 | 0.050 | 0.050 |
| FD&C Blue #1 (1% Sol'n) | 0.075 | 0.075 | 0.075 |
| Part 5- Second Premix | | | |
| Propylene Glycol | 8.000 | 8.000 | 8.000 |
| CAP Betaine | 1.250 | 8.300 | 2.000 |
| Polysorbate 20 | 1.250 | 0.600 | 2.880 |
| Flavour | 0.700 | 0.700 | 0.700 |
| SLS | 0.600 | 0.600 | 0.600 |
| Part 6- Aesthetics | | | |
| BFG50- Silica | — | 0.05 | 0.05 |
| TOTAL = | 100 | 100 | 100 |
| 1 week, 49° C. | | | |
| Visuals | Clear, No Silica | Clear, Silica Suspended | Clear, Silica Settled |
| pH | 5.45 | 5.40 | 5.46 |
| Viscosity (cps) | 140 | 400 | 20 |
| Shakefoam (0.1% MW Solution, ml) | 175 | 200 | 175 |
| 2 months, 49° C. | | | |
| Structure | No Silica | Silica Suspended | Silica Settled |
| Colour Change (Blue to Green) | Slight | Moderate | Complete |

|  | D | E | F | G |
|---|---|---|---|---|
| Part 1 | | | | |
| Qs Hot Deionised Water | 34.785 | 32.699 | 31.682 | 33.849 |
| Part 2- First Premix | | | | |
| Glycerine | 9.000 | 9.000 | 9.000 | 9.000 |
| Xanthan Gum | 0.247 | 0.350 | 0.050 | 0.050 |
| Sodium CMC Gum | 0.010 | 0.062 | 0.010 | 0.010 |

TABLE 1-continued

| Part 3 | | | | |
|---|---|---|---|---|
| Sorbitol | 30.000 | 30.000 | 30.000 | 30.000 |
| Pluronic F-127NF (Poloxomer) | 0.250 | 0.250 | 0.250 | 0.713 |
| Part 4- Third Premix | | | | |
| Hot Deionised Water | 10.000 | 10.000 | 10.000 | 10.000 |
| Sodium Benzoate | 0.500 | 0.500 | 0.500 | 0.500 |
| Monobasic Na Phosphate | 1.000 | 1.000 | 1.000 | 1.000 |
| Saccharin | 0.050 | 0.050 | 0.050 | 0.050 |
| CPC | 0.050 | 0.050 | 0.050 | 0.050 |
| FD&C Blue #1 (1% Sol'n) | 0.075 | 0.075 | 0.075 | 0.075 |
| Part 5- Second Premix | | | | |
| Propylene Glycol | 8.000 | 8.000 | 8.000 | 8.000 |
| CAP Betaine | 2.000 | 4.980 | 6.433 | 3.337 |
| Polysorbate 20 | 1.733 | 1.634 | 0.600 | 2.016 |
| Flavour | 0.700 | 0.700 | 0.700 | 0.700 |
| SLS | 0.600 | 0.600 | 0.600 | 0.600 |
| Part 6- Aesthetics | | | | |
| BFG50- Silica | 1 | 0.05 | 1 | 0.05 |
| TOTAL | 100 | 100 | 100 | 100 |
| 1 week, 49° C. | | | | |
| Visuals | Clear, Silica Settled | Clear, Silica Suspended | Clear, Silica Settled | Clear, Silica Settled |
| pH | 5.45 | 5.45 | 5.38 | 5.44 |
| Viscosity (cps) | 160 | 420 | 20 | 20 |
| Shakefoam (0.1% MW Solution, ml) | 160 | 265 | 190 | 180 |
| 2 months, 49° C. | | | | |
| Structure | Silica Settled | Silica Suspended | Silica Settled | Silica Settled |
| Colour Change (Blue to Green) | Slight | Slight | Moderate | Complete |

| | H | I | J | K |
|---|---|---|---|---|
| Part 1 | | | | |
| Qs Hot Deionised Water | 32.573 | 32.573 | 31.808 | 34.785 |
| Part 2- First Premix | | | | |
| Glycerine | 9.000 | 9.000 | 9.000 | 9.000 |
| Xanthan Gum | 0.204 | 0.068 | 0.050 | 0.050 |
| Sodium CMC Gum | 0.068 | 0.204 | 0.100 | 0.100 |
| Part 3 | | | | |
| Sorbitol | 30.000 | 30.000 | 30.000 | 30.000 |
| Pluronic F-127NF (Poloxomer) | 0.944 | 0.944 | 0.250 | 0.250 |
| Part 4- Third Premix | | | | |
| Hot Deionised Water | 10.000 | 10.000 | 10.000 | 10.000 |
| Sodium Benzoate | 0.500 | 0.500 | 0.500 | 0.500 |
| Monobasic Na Phosphate | 1.000 | 1.000 | 1.000 | 1.000 |
| Saccharin | 0.050 | 0.050 | 0.050 | 0.050 |
| CPC | 0.050 | 0.050 | 0.050 | 0.050 |
| FD&C Blue #1 (1% Sol'n) | 0.075 | 0.075 | 0.075 | 0.075 |
| Part 5- Second Premix | | | | |
| Propylene Glycol | 8.000 | 8.000 | 8.000 | 8.000 |
| CAP Betaine | 5.160 | 5.160 | 6.253 | 2.000 |
| Polysorbate 20 | 0.600 | 0.600 | 1.389 | 1.840 |
| Flavour | 0.700 | 0.700 | 0.700 | 0.700 |
| LS | 0.600 | 0.600 | 0.600 | 0.600 |
| Part 6- Aesthetics | | | | |
| BFG50- Silica | 0.476 | 0.476 | 0.175 | 1 |
| TOTAL | 100 | 100 | 100 | 100 |
| 1 week, 49° C. | | | | |
| Visuals | Clear, Silica Settled | Clear, Silica Settled | Clear, Silica Settled | Clear, Silica Settled |
| pH | 5.42 | 5.42 | 5.41 | 5.44 |
| Viscosity (cps) | 160 | 40 | 20 | 20 |

TABLE 1-continued

|  |  |  |  |  |
|---|---|---|---|---|
| Shakefoam (0.1% MW Solution, ml) | 200 | 225 | 200 | 150 |
| 2 months, 49° C. |  |  |  |  |
| Structure | Silica Settled Slight | Silica Settled Moderate | Silica Settled Complete | Silica Settled Moderate |
| Colour Change (Blue to Green) |  |  |  |  |

|  | L | M | N | O |
|---|---|---|---|---|
| Part 1 |  |  |  |  |
| Qs Hot Deionised Water | 34.785 | 34.785 | 34.785 | 34.785 |
| Part 2- First Premix |  |  |  |  |
| Glycerine | 9.000 | 9.000 | 9.000 | 9.000 |
| Xanthan Gum | 0.050 | 0.164 | 0.173 | 0.050 |
| Sodium CMC Gum | 0.100 | 0.100 | 0.100 | 0.010 |
| Part 3 |  |  |  |  |
| Sorbitol | 30.000 | 30.000 | 30.000 | 30.000 |
| Pluronic F-127NF (Poloxomer) | 1.932 | 1.376 | 0.250 | 2.000 |
| Part 4- Third Premix |  |  |  |  |
| Hot Deionised Water | 10.000 | 10.000 | 10.000 | 10.000 |
| Sodium Benzoate | 0.500 | 0.500 | 0.500 | 0.500 |
| Monobasic Na Phosphate | 1.000 | 1.000 | 1.000 | 1.000 |
| Saccharin | 0.050 | 0.050 | 0.050 | 0.050 |
| CPC | 0.050 | 0.050 | 0.050 | 0.050 |
| FD&C Blue #1 (1% Sol'n) | 0.075 | 0.075 | 0.075 | 0.075 |
| Part 5- Second Premix |  |  |  |  |
| Propylene Glycol | 8.000 | 8.000 | 8.000 | 8.000 |
| CAP Betaine | 2.000 | 2.000 | 2.000 | 2.000 |
| Polysorbate 20 | 1.108 | 0.600 | 2.667 | 0.600 |
| Flavour | 0.700 | 0.700 | 0.700 | 0.700 |
| SLS | 0.600 | 0.600 | 0.600 | 0.600 |
| Part 6- Aesthetics |  |  |  |  |
| BFG50- Silica | 0.05 | 1 | 0.05 | 0.58 |
| TOTAL | 100 | 100 | 100 | 100 |
| 1 week, 49° C. |  |  |  |  |
| Visuals | Clear, Silica Settled | Clear, Silica Settled | Clear, Silica Settled | Clear, Silica Settled |
| pH | 5.47 | 5.44 | 5.47 | 5.48 |
| Viscosity (cps) | 20 | 100 | 140 | 0 |
| Shakefoam (0.1% MW Solution, ml) | 190 | 175 | 160 | 160 |
| 2 months, 49° C. |  |  |  |  |
| Structure | Silica Settled Slight | Silica Settled Slight | Silica Settled Moderate | Silica Settled Moderate |
| Colour Change (Blue to Green) |  |  |  |  |

|  | P | Q | R | S |
|---|---|---|---|---|
| Part 1 |  |  |  |  |
| Qs Hot Deionised Water | 34.785 | 33.164 | 32.573 | 30.086 |
| Part 2- First Premix |  |  |  |  |
| Glycerine | 9.000 | 9.000 | 9.000 | 9.000 |
| Xanthan Gum | 0.350 | 0.050 | 0.204 | 0.316 |
| Sodium CMC Gum | 0.100 | 0.062 | 0.068 | 0.010 |
| Part 3 |  |  |  |  |
| Sorbitol | 30.000 | 30.000 | 30.000 | 30.000 |
| Pluronic F-127NF (Poloxomer) | 0.868 | 1.074 | 0.944 | 0.250 |
| Part 4- Third Premix |  |  |  |  |
| Hot Deionised Water | 10.000 | 10.000 | 10.000 | 10.000 |
| Sodium Benzoate | 0.500 | 0.500 | 0.500 | 0.500 |
| Monobasic Na Phosphate | 1.000 | 1.000 | 1.000 | 1.000 |
| Saccharin | 0.050 | 0.050 | 0.050 | 0.050 |
| CPC | 0.050 | 0.050 | 0.050 | 0.050 |
| FD&C Blue #1 (1% Sol'n) | 0.075 | 0.075 | 0.075 | 0.075 |

TABLE 1-continued

|  |  |  |  |  |
|---|---|---|---|---|
| Part 5- Second Premix |  |  |  |  |
| Propylene Glycol | 8.000 | 8.000 | 8.000 | 8.000 |
| CAP Betaine | 2.000 | 4.317 | 5.160 | 8.713 |
| Polysorbate 20 | 1.453 | 1.293 | 0.600 | 0.600 |
| Flavour | 0.700 | 0.700 | 0.700 | 0.700 |
| SLS | 0.600 | 0.600 | 0.600 | 0.600 |
| Part 6- Aesthetics |  |  |  |  |
| BFG50- Silica | 0.469 | 0.065 | 0.476 | 0.05 |
| TOTAL | 100 | 100 | 100 | 100 |
| 1 week, 49° C. |  |  |  |  |
| Visuals | Clear, Silica Suspended | Clear, Silica Settled | Clear, Silica Settled | Clear, Silica Suspended |
| pH | 5.44 | 5.44 | 5.43 | 5.38 |
| Viscosity (cps) | 360 | 0 | 120 | 300 |
| Shakefoam (0.1% MW Solution, ml) | 195 | 175 | 200 | 230 |
| 2 months, 49° C. |  |  |  |  |
| Structure | Silica Suspended | Silica Settled | Hazy, Silica Settled | Silica Suspended |
| Colour Change (Blue to Green) | Very Slight | Moderate | Moderate | Very Slight |

|  | T | U | V | W |
|---|---|---|---|---|
| Part 1 |  |  |  |  |
| Qs Hot Deionised Water | 32.699 | 31.966 | 34.785 | 34.458 |
| Part 2- First Premix |  |  |  |  |
| Glycerine | 9.000 | 9.000 | 9.000 | 9.000 |
| Xanthan Gum | 0.350 | 0.050 | 0.178 | 0.350 |
| Sodium CMC Gum | 0.062 | 0.010 | 0.010 | 0.100 |
| Part 3 |  |  |  |  |
| Sorbitol | 30.000 | 30.000 | 30.000 | 30.000 |
| Pluronic F-127NF (Poloxomer) | 0.250 | 1.322 | 1.580 | 2.000 |
| Part 4- Third Premix |  |  |  |  |
| Hot Deionised Water | 10.000 | 10.000 | 10.000 | 10.000 |
| Sodium Benzoate | 0.500 | 0.500 | 0.500 | 0.500 |
| Monobasic Na Phosphate | 1.000 | 1.000 | 1.000 | 1.000 |
| Saccharin | 0.050 | 0.050 | 0.050 | 0.050 |
| CPC | 0.050 | 0.050 | 0.050 | 0.050 |
| FD&C Blue #1 (1% Sol'n) | 0.075 | 0.075 | 0.075 | 0.075 |
| Part 5- Second Premix |  |  |  |  |
| Propylene Glycol | 8.000 | 8.000 | 8.000 | 8.000 |
| CAP Betaine | 4.980 | 6.027 | 2.000 | 2.467 |
| Polysorbate 20 | 1.634 | 0.600 | 1.422 | 0.600 |
| Flavour | 0.700 | 0.700 | 0.700 | 0.700 |
| SLS | 0.600 | 0.600 | 0.600 | 0.600 |
| Part 6- Aesthetics |  |  |  |  |
| BFG50- Silica | 0.05 | 0.05 | 0.05 | 0.05 |
| TOTAL | 100 | 100 | 100 | 100 |
| 1 week, 49° C. |  |  |  |  |
| Visuals | Clear, Silica Suspended | Clear, Silica Settled | Clear, Silica Suspended | Clear, Silica Suspended |
| pH | 5.48 | 5.46 | 5.48 | 5.47 |
| Viscosity (cps) | 400 | 40 | 140 | 320 |
| Shakefoam (0.1% MW Solution, ml) | 200 | 225 | 170 | 210 |
| 2 months, 49° C. |  |  |  |  |
| Structure | Silica Suspended | Silica Settled | Silica Suspended | Silica Suspended |
| Colour Change (Blue to Green) | Very Slight | Moderate | Very Slight | Very Slight |

|  | X | Y | Z |
|---|---|---|---|
| Part 1 |  |  |  |
| Qs Hot Deionised Water | 29.582 | 33.251 | 36.51 |

TABLE 1-continued

| Part 2- First Premix | | | |
|---|---|---|---|
| Glycerine | 9.000 | 9.000 | 9.000 |
| Xanthan Gum | 0.050 | 0.050 | 0.170 |
| Sodium CMC Gum | 0.060 | 0.010 | 0.070 |
| Part 3 | | | |
| Sorbitol | 30.000 | 30.000 | 30.000 |
| Pluronic F-127NF (Poloxomer) | 0.250 | 0.488 | 0.850 |
| Part 4- Third Premix | | | |
| Hot Deionised Water | 10.000 | 10.000 | 10.000 |
| Sodium Benzoate | 0.500 | 0.500 | 0.500 |
| Monobasic Na Phosphate | 1.000 | 1.000 | 1.000 |
| Saccharin | 0.050 | 0.050 | 0.050 |
| CPC | 0.050 | 0.050 | 0.050 |
| FD&C Blue #1 (1% Sol'n) | 0.075 | 0.075 | 0.075 |
| Part 5- Second Premix | | | |
| Propylene Glycol | 8.000 | 8.000 | 8.000 |
| CAP Betaine | 9.433 | 4.193 | 1.250 |
| Polysorbate 20 | 0.600 | 1.286 | 1.250 |
| Flavour | 0.700 | 0.700 | 0.700 |
| SLS | 0.600 | 0.600 | 0.600 |
| Part 6- Aesthetics | | | |
| BFG50- Silica | 0.05 | 0.747 | — |
| TOTAL | 100 | 100 | 100 |
| 1 week, 49° C. | | | |
| Visuals | Clear, Silica Settled | Clear, Silica Settled | Clear, No Silica |
| pH | 5.39 | 5.42 | 5.48 |
| Viscosity (cps) | 0 | 0 | 120 |
| Shakefoam (0.1% MW Solution, ml) | 210 | 270 | 185 |
| 2 months, 49° C. | | | |
| Structure | Silica Settled | Silica Settled | N/A |
| Colour Change (Blue to Green) | Moderate | Moderate | N/A |

Example 2

Optical density is used to evaluate the clarity of a first composition (Composition I) prepared in accordance with an exemplary method of the present invention and a second composition (Comparative Example I) prepared by a conventional process. A sample of Composition I and a sample of Comparative Example I are placed in a cuvette and placed in a X-RITE UV-Vis spectrophotometer. The absorbance spectrum is measured at 500 nm for both samples. The results of this comparison are described in Table 2.

TABLE 2

| Composition | Optical Density at 500 nm |
|---|---|
| Composition I | 0.05988 |
| Comparative Example I | 0.14590 |

Whilst particular embodiments of the invention have been illustrated and described, it will be obvious to those skilled in the art that various changes and modifications may be made without departing from the scope of the invention as defined in the appended claims.

We claim:

1. A process for preparing an alcohol-free aqueous liquid toothpaste composition which is usable as a mouthwash, the liquid toothpaste being an oil-in-water emulsion with a clear appearance and a viscosity of between 60 and 550 cps, the process comprising:

(i) preparing a first premix by combining at least one gum with a first humectant in a first vessel, wherein the first humectant is glycerin;
(ii) preparing a second premix by:
   adding a betaine surfactant, a polysorbate surfactant, and a water-insoluble flavouring agent to a second vessel containing an alkylene glycol;
   mixing the contents of the second vessel; and
   adding an anionic surfactant to the second vessel;
(iii) preparing a third premix by combining water, a preservative, and an active agent in a third vessel, and wherein the water is present at 2 wt % to 15 wt % of the third premix;
(iv) adding the first premix to a fourth vessel containing preheated water and mixing the contents of the fourth vessel;
(v) adding a second humectant to the fourth vessel and mixing, wherein the second humectant is sorbitol;
(vi) adding a nonionic block copolymer to the fourth vessel and mixing;
(vii) adding the third premix to the fourth vessel and mixing; and
(viii) adding the second premix to the fourth vessel and mixing;
wherein the second premix is an oil-phase premix, and the mixing in step (viii) produces an oil-in-water emulsion;
wherein the flavouring agent is present in an amount of 0.5 wt. % to 5 wt. % based on the total weight of the composition;

wherein the betaine surfactant is a an alkyl dimethyl betaine and is present in an amount of between 1 wt. % and 10 wt. % based on the total weight of the composition;

wherein the polysorbate surfactant is present in an amount of between 0.5 wt. % and 3 wt. % based on the total weight of the composition;

wherein the alkylene glycol is selected from ethylene glycol, propylene glycol, dipropylene glycol, hexylene glycol and mixtures thereof, and is present in an amount of between 5 wt % and 10 wt % based on the total weight of the composition;

wherein the anionic surfactant is present in an amount of between 0.5 wt. % and 2 wt. % based on the total weight of the composition;

wherein the nonionic block copolymer is a poloxamer and is present in an amount of between 0.25 wt. % and 2 wt. % based on the total weight of the composition.

2. The process of claim 1, wherein the composition has an optical density of less than 0.1 at 500 nm.

3. The process of claim 1, wherein the composition has an optical density of less than 0.075 at 500 nm.

4. The process of claim 1 further comprising, after step (viii), the step of:

(ix) adding silica to the fourth vessel and mixing.

5. The process of claim 1 wherein the first humectant is present in an amount of between 5 wt. % and 20 wt. % based on the total weight of the composition.

6. The process of claim 1 wherein the second humectant is present in an amount of between 15 wt. % and 45 wt. % based on the total weight of the composition.

7. The process of claim 1 wherein the total amount of the at least one gum is 0.01 wt. % to 2 wt. % based on the total weight of the composition.

8. The process of claim 1 wherein the at least one gum is selected from gum-type colloidal polymers and cellulosic polymers, and combinations thereof.

9. The process of claim 8 wherein the colloidal polymer is selected from agar, agarose, albumin, algae colloid, alginates, alginic acid and salts thereof, amber, ammoniac, amylopectins, arabinans, arabinogalactan, arabinoxylans, asafetida, bdellium, carageenans, casein, chicle, collagen, copal, curdlan, dermatin sulfate, dextrans, cross-linked dextrans, dextrin, emulsan, gelatin, fenugreek, frankincense, furcellarans, galactoglucomannans, galactomannans, gamboge, gellan, gellan gum, glucomannans, glycogens, guar, guar gum, hydroxypropylated guar gums, carboxymethyl guar gum, carboxymethyl(hydroxypropyl) guar gum, hydroxyethyl guar gum, gum arabic, gum elastic, gum ghatti, gum karaya, gum tragancanth (tragacanthin), heparin, hyaluronic acid, India rubber, inulin, karaya gum, keratin sulfate, konjac flour, konjac mannan, labdanum, laminarans, laurdimonium, acidic laxseed saccharide, levan, locust bean gum, myrrh, okra gum, pectic acids, pectin, polydextrose, polyquaternium-4, polyquaternium-10, polyquaternium-28, protopectins, psyllium seed gum, pullulan, quince seed gum, sodium hyaluronate, raffinose, rhamsan, scleroglucan, sodium alginate, stachylose, starch from rice, corn, potato or wheat, tapioca starch, succinoglycan, tamarind seed gum, trant gum, water-soluble soybean polysaccharide, whelan, xanthan, xanthan gum, xylans, xyloglucans, and mixtures thereof.

10. The process of claim 8 wherein the cellulosic polymer is selected from cellulose; methyl cellulose; ethyl cellulose; propyl cellulose; butyl cellulose; carboxymethyl cellulose; carboxyethyl cellulose; carboxymethyl methyl cellulose; carboxyethyl ethyl cellulose; carboxymethyl methyl cellulose; carboxymethyl ethyl cellulose; hydroxyalkyl cellulose; hydroxymethyl cellulose; hydroxyethyl cellulose; hydroxypropyl cellulose; hydroxybutyl cellulose; hydroxymethyl methyl cellulose; hydroxyethyl methyl cellulose; hydroxypropyl methyl cellulose; hydroxybutyl methyl cellulose; hydroxymethyl ethyl cellulose; hydroxyethyl ethyl cellulose; hydroxypropyl ethyl cellulose; hydroxybutyl ethyl cellulose; hydroxymethyl propyl cellulose; hydroxyethyl propyl cellulose; hydroxypropyl propyl cellulose; hydroxybutyl propyl cellulose; hydroxymethyl butyl cellulose; hydroxyethyl butyl cellulose; hydroxypropyl butyl cellulose; hydroxybutyl butyl cellulose; hydroxypropyl oxyethyl cellulose; steardimonium hydroxyethyl cellulose; cocodimonium hydroxypropyl oxyethyl cellulose; sodium carboxymethyl cellulose; nitrocellulose; sodium cellulose sulfate; chondroitin; chitin; chitosan; chitosan pyrrolidone carboxylate; chitosan glycolate chitosan lactate and mixtures thereof.

11. The process of claim 8, wherein the at least one gum comprises xanthan gum and a cellulosic polymer.

12. The process of claim 11, wherein the cellulosic polymer is sodium carboxymethyl cellulose.

13. The process of claim 1 wherein the betaine surfactant is cocoamidoethyl betaine, cocoamidopropyl betaine, lauramidopropyl betaine or mixtures thereof.

14. The process of claim 13 wherein the betaine surfactant is cocoamidopropyl betaine.

15. The process of claim 1 wherein the polysorbate surfactant is selected from polysorbate 20, polysorbate 40, polysorbate 60, polysorbate 80 and mixtures thereof.

16. The process of claim 15 wherein the polysorbate surfactant is polysorbate 20.

17. The process of claim 1 wherein the alkylene glycol is propylene glycol.

18. The process of claim 1 wherein the anionic surfactant is sodium lauryl sulfate.

19. The process of claim 1 wherein the preservative is present in an amount of between 0.1 wt. % and 1 wt. % based on the total weight of the composition.

20. The process of claim 1 wherein the preservative is selected from parabens, potassium sorbate, benzyl alcohol, phenoxyethanol, polyaminopropyl biguanide, caprylic acid, sodium benzoate and mixtures thereof.

21. The process of claim 20 wherein the preservative is sodium benzoate.

22. The process of claim 1 wherein the active agent is selected from an antimicrobial agent, a tartar control agent, a fluoride ion source, a breath-freshening agent, an antioxidant, a saliva stimulating agent, an antiplaque agent, a desensitizing agent, and mixtures thereof.

23. The process of claim 22 wherein the active agent comprises an antimicrobial agent, the antimicrobial agent being selected from cetylpyridinium chloride, triclosan, zinc ion sources, stannous ion sources, chlorhexidine, benzalkonium chloride, and mixtures thereof.

24. The process of claim 22, wherein the active agent comprises a tartar control agent, the tartar control agent being selected from monobasic sodium phosphate, dibasic sodium phosphate, tribasic sodium phosphate, sodium tripolyphosphate, sodium tetrapolyphosphate, mono-, di-, tri- and tetrasodium pyrophosphates, sodium trimetaphosphate, sodium hexametaphosphate, monobasic potassium phosphate, dibasic potassium phosphate, tribasic potassium phosphate, potassium tripolyphosphate, potassium tetrapolyphosphate, mono-, di-, tri- and tetrapotassium pyrophosphates, potassium trimetaphosphate, potassium hexametaphosphate, monobasic ammonium phosphate, dibasic ammonium phosphate, tribasic ammonium phosphate, ammonium tripolyphosphate, ammonium tetrapolyphosphate, mono-, di-, tri- and tetraammonium pyrophosphates, ammonium trimetaphosphate, ammonium hexametaphosphate and mixtures thereof.

25. The process of claim 1, wherein the preheated water in step (iv) is heated to between 66° C. and 99° C. (between 150° F. and 210° F.).

26. The process of claim 1, wherein the water in step (iii) is heated to between 66° C. and 99° C. (between 150° F. and 210° F.).

27. The process of claim 1 wherein the betaine surfactant, polysorbate surfactant and water-insoluble flavouring agent are added to the vessel in step (ii) in the following order:
  I) betaine surfactant,
  II) polysorbate surfactant,
  III) flavouring agent.

28. The process of claim 1 wherein the contents of the fourth vessel in step (iv) are mixed for between 10 minutes and 20 minutes.

29. The process of claim 1 wherein the mixing of step (vi) is carried out under vacuum at a pressure of from about 25 to about 28 in. Hg.

\* \* \* \* \*